US005245022A

United States Patent [19]
Weis et al.

[11] Patent Number: 5,245,022
[45] Date of Patent: Sep. 14, 1993

[54] EXONUCLEASE RESISTANT TERMINALLY SUBSTITUTED OLIGONUCLEOTIDES

[75] Inventors: Alexander L. Weis, Berwyn, Pa.; Fred T. Oakes, Rochester, N.Y.; Frederick H. Hausheer, San Antonio, Tex.; Paul F. Cavanaugh, Jr., West Chester; Patricia S. Moskwa, Phoenixville, both of Pa.

[73] Assignee: Sterling Drug, Inc., New York, N.Y.

[21] Appl. No.: 562,180

[22] Filed: Aug. 3, 1990

[51] Int. Cl.$^5$ .......................................... C07H 21/00
[52] U.S. Cl. ................................. 536/24.5; 536/25.32
[58] Field of Search .............................. 536/27–29; 514/44

[56] References Cited
PUBLICATIONS

Stirchak et al., "Uncharged Stereoregular Nucleic Acid Analogues. I. Synthesis of a Cytosine-Containing Oligomer with Carbamate Internucleoside Linkages", J. Org. Chem., 52, 4202–4206 (1987).
Mungall et al., "Carbamate Analogues of Oligonucleotides", J. Org. Chem., vol. 42, No. 4, 1977, pp. 703–706.
Coull et al., "Synthesis and Characterization of a Carbamate-Linked Oligonucleoside", Tetrahedron Letters, vol. 28, No. 7, pp. 745–748, 1987.
Schneider et al., "Building Blocks for Oligonucleotide Analogs with Dimethylene-Sulfide, —Sulfoxide, and —Sulfone Groups Replacing Phosphodiester Linkages", Tetrahedron Letters, vol. 31, No. 3, pp. 335–338, 1990.
Ogilvie et al., "Synthesis of a Thymidine Dinucleotide Analogue Containing an Internucleotide Silyl Linkage", Tetrahedon Letters, vol. 26, No. 35, pp. 4159–4162, 1985.
Cormier et al., "Synthesis of Hexanucleotide Analogues Containing Diisopropylsilyl Internucleotide Linkages", Nucleic Acids Research, vol. 16, No. 10, pp. 4583–4594, 1988.

*Primary Examiner*—John W. Rollins
*Assistant Examiner*—L. Eric Crane
*Attorney, Agent, or Firm*—Irving Newman

[57] ABSTRACT

Compounds, compositions and methods for inhibiting gene expression are disclosed. The compounds comprise oligonucleotide sequences of from about 9 to about 200 bases having a diol at either or both termini. Preferred diols are polyalkyleneglycols, preferably polyethyleneglycols. Pharmaceutical compositions comprising the compounds and a physiologically acceptable carrier and methods of inhibiting gene expression in mammals comprising administering such compounds are also provided. Methods for inhibiting nuclease cleavage of compounds are also provided.

26 Claims, No Drawings

EXONUCLEASE RESISTANT TERMINALLY SUBSTITUTED OLIGONUCLEOTIDES

FIELD OF THE INVENTION

The present invention relates to compounds, compositions and methods for inhibiting gene expression. The compounds of this invention are nuclease resistant compounds of oligonucleotide sequences of from about 9 to about 200 bases that have a diol at either or both termini. The present invention further relates to methods for making compounds that are resistant to cleavage by nuclease enzymes.

BACKGROUND OF THE INVENTION

Antisense compounds contain oligonucleotides that bind to or hybridize with a complementary nucleotide sequence in another nucleic acid, RNA or DNA, to inhibit the function or synthesis of said nucleic acid. Because of their ability to hybridize with both RNA and DNA, antisense compounds can interfere with gene expression at the level of transcription, RNA processing or translation.

Antisense compounds can be designed and synthesized to prevent the transcription of specific genes to RNA by hybridizing with genomic DNA and directly or indirectly inhibiting the action of RNA polymerase. An advantage of targeting DNA is that only small amounts of antisense compounds are needed to achieve a therapeutic effect. Alternatively, antisense compounds can be designed and synthesized to hybridize with RNA to inhibit post-transcriptional modification (RNA processing) or protein synthesis (translation) mechanisms. Exemplary target RNAs are messenger RNA (mRNA), transfer RNA (tRNA), ribosomal RNA (rRNA) and the like. Examples of processing and translation mechanisms include splicing of pre-mRNA to remove introns, capping of the 5' terminus of mRNA, hybridization arrest and nuclease mediated mRNA hydrolysis.

At the present time, however, the development of practical scientific and therapeutic applications of antisense technologies is hampered by a number of technical problems. Klausner, A., Biotechnology, 8:303-304 (1990). Synthetic antisense molecules are susceptible to rapid degradation by nucleases that exist in target cells. The oligonucleotide sequences of antisense DNA or RNA, for example, are destroyed by exonucleases acting at either the 5' or 3' terminus of the nucleic acid. In addition, endonucleases can cleave the DNA or RNA at internal phosphodiester linkages between individual nucleotides. As a result of such cleavage, the effective half-life of administered antisense compounds is very short necessitating the use of large, frequently administered dosages.

Another problem is the extremely high cost of producing antisense compounds using available semiautomatic nucleic acid synthesizers. It has recently been estimated that the cost of producing one gram of antisense DNA is about $100,000. Armstrong, L., *Business Week*, Mar. 5, 1990, page 89.

A further problem relates to the delivery of antisense agents to desired targets within the body and cell. Antisense agents targeted to genomic DNA must gain access to the nucleus (i.e. the agents must permeate the plasma and nuclear membrane). The need for increased membrane permeability (increased hydrophobicity) must be balanced, however, against the need for aqueous solubility (increased hydrophilicity) in body fluid compartments such as the plasma and cell cytosol.

A still further problem relates to the stability of antisense agents whether free within the body or hybridized to target nucleic acids. Oligonucleotides such as antisense DNA or RNA are susceptible to unstable steric reconfiguration around chiral phosphate centers.

Gene targeting via antisense agents is the inevitable next step in human therapeutics. Armstrong, supra at 88. The successful application of antisense technology to the treatment of disease however, requires finding solutions to the problems set forth above. The present invention provides compounds, compositions and methods for inhibiting nuclease degradation of antisense compounds.

SUMMARY OF THE INVENTION

The present invention provides nuclease resistant compounds comprising oligonucleotide sequences of from about 9 to about 200 bases having a diol at either or both termini.

Preferred diols are 1,2-diols (glycols). Representative glycols are polyalkyleneglycols, preferably, polyethyleneglycols or polypropyleneglycols. Preferred glycols are tetraethyleneglycol and hexaethyleneglycol. Suitable diols may also include polyols that have all but two hydroxyls blocked.

More particuarly, compounds of this invention comprise oligonucleotides of the formula:

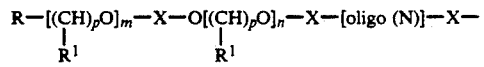

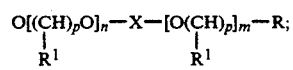

where

R is OH, SH, NR$^2$R$^3$ wherein R$^2$ and R$^3$ are independently hydrogen or C$_1$-C$_6$ alkyl, or NHR$^4$ wherein R$^4$ is C$_1$-C$_{12}$acyl;

R$^1$ is hydrogen or C$_1$-C$_{12}$ alkyl;

X =

oligo (N) is an oligonucleotide sequence of from about 9 to about 200 bases;

m is independently 0 to 50 with the proviso that at least one m be 1 to 50;

n is independently 0 to 50; and p is independently 0 to 4 with the proviso that at least one p be 2 to 4.

In a preferred embodiment, the oligonucleotide contains, in a homopolymer or heteropolymer sequence, any combination of dA, dC, dG, T.

Where the glycol is polyethyleneglycol, the compounds of the present invention comprise oligonucleotides of the formula:

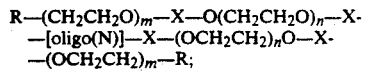

where

R is OH, SH, NR$^2$R$^3$ wherein R$^2$ and R$^3$ are independently hydrogen or C$_1$–C$_6$ alkyl, or NHR$^4$ wherein R$^4$ is C$_1$–C$_{12}$ acyl;

X=

oligo N is an oligonucleotide sequence of from about 9 to about 50 bases;

m is independently 0 to 50 with the proviso that at least one m be 1 to 50; and n is independently 0 to 50.

The present invention further provides a method of inhibiting nuclease degradation of compounds comprising attaching a diol to either the 5', the 3' terminus or both termini of said compound. The diols are attached to the 5' and/or the 3' terminus by reacting the oligonucleotide sequences with an alkoxytrityldiolcyanophosphine, preferably a dimethoxytritylglycolcyanophosphine or a monomethoxytritylglycolcyanophosphine.

This invention also provides pharmaceutical compositions comprising compounds comprising oligonucleotide sequences of from about 9 to about 200 bases having a diol at either or both termini and a physiologically acceptable carrier.

The present invention further provides a method of inhibiting gene expression comprising administering to a mammal an effective amount of a compound comprising an oligonucleotide sequence of from about 9 to about 200 bases having a diol at either or both termini.

DETAILED DESCRIPTION OF THE INVENTION

The compounds of the present invention comprise oligonucleotides of from about 9 to about 200 bases having a diol at either or both termini. Preferred diols are glycols, also known as 1,2-diols, which contain two hydroxyl groups on adjacent carbons. Preferred glycols are polyalkyleneglycols. The term "alkylene" as used herein. refers to linear and branched chain radicals having 2 to 4 carbon atoms which may be optionally substituted as herein defined. Representative of such radicals are, ethylene, propylene, isobutylene, and the like. Preferred polyalkyleneglycols are polyethyleneglycols. More preferred are tetraethyleneglycol and hexaethyleneglycol.

The diols are attached to either the 5', the 3' or both termini of the oligonucleotides via phosphodiester linkages. In one embodiment, the diols are attached to only one terminus of an oligonucleotide sequence.

The terminal diol is linked to a moiety selected from the group consisting of hydroxyl (OH), sulfhydryl (SH), amino (NH$_2$), alkylamino (NH-alkyl), dialkylamino (N[alkyl]$_2$) and amido (NH[acyl]). As used herein, "alkyl" refers to linear or branched chain radicals having 1 to 12 carbon atoms which may be optionally substituted as herein defined. Representative alkyl and dialkylamino radicals include methyl-, ethyl-, propyl-, butyl-, pentyl-, hexyl-, dimethyl-, diethyl-, dipropyl-, dibutyl-, dipentyl- and dihexylamines and the like. As used herein, "NH(acyl)" or "amido" refers to linear or branched chain radicals having 1 to 12 carbon atoms with a terminal O=CNH$_2$ group. Representative amido radicals include methanamide, ethanamide, propanamide, butanamide, pentanamide, hexanamide, heptanamide, octanamide, nonanamide, decanamide, undecanamide and dodecanamide.

The compounds of the present invention comprise oligonucleotides of the formula:

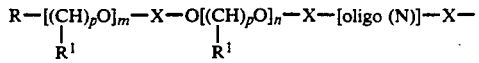
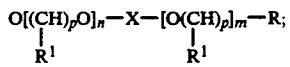

where

R is OH, SH, NR$^2$R$^3$ wherein R$^2$ and R$^3$ are independently hydrogen or C$_1$–C$_6$ alkyl, or NHR$^4$ wherein R$^4$ is C$_1$–C$_{12}$ acyl;

R$^1$ is hydrogen or C$_1$–C$_{12}$ alkyl;

X=

oligo (N) is an oligonucleotide sequence of from about 9 to about 200 bases;

m is independently 0 to 50 with the proviso that at least one m be 1 to 50;

n is independently 0 to 50; and p is independently 0 to 4 with the proviso that at least one p be 2 to 4.

The oligonucleotide sequence is preferably a homopolymer or heteropolymer sequence containing any combination of dA, dC, dG, T or analogs thereof.

In a preferred embodiment, m and n are independently 1 to 8 and, more preferably both are 4. Preferred oligonucleotide sequences contain from about 9 to about 50 bases, more preferably about 12 to about 25 bases, and most preferably about 15 to about 18 bases.

In a preferred embodiment, the antisense compounds have polyethyleneglycols (PEGs) at both the 5' and 3' termini and have the formula:

R—(CH$_2$CH$_2$O)$_m$—X—O(CH$_2$CH$_2$O)$_n$—X-
—[oligo(N)]—X—(OCH$_2$CH$_2$)$_n$O
—X—(OCH$_2$CH$_2$)$_m$—R;

where

R is OH, SH, NR$^2$R$^3$ wherein R$^2$ and R$^3$ are independently hydrogen or C$_1$–C$_6$ alkyl, or NHR$^4$ wherein R$^4$ is C$_1$–C$_{12}$ acyl;

X=

oligo N is an oligonucleotide sequence of from about 9 to about 200 bases;

m is independently 0 to 50 with the proviso that at least one m be 1 to 50; and n is independently 0 to 50.

In preferred embodiments, the polyethyleneglycol is tetraethyleneglycol (TEG) and both m and n are 4 or hexaethyleneglycol and both m and n are 6.

The compounds of the present invention are useful as antisense agents. Antisense compounds contain oligonucleotide sequences that hybridize with a complementary nucleotide sequence in another target nucleic acid to inhibit the translational or transcriptional function of said target nucleic acid. The target nucleic acid may be either RNA or DNA.

Antisense DNA compounds of the present invention comprise oligonucleotides of from about 9 to about 200 bases having homopolymer or heteropolymer sequences of deoxynucleotides selected from the group consisting of deoxyadenylic acid (dA), deoxycytidylic acid (dC), deoxyguanylic acid (dG) or thymidylic acid (T).

Antisense RNA compounds of the present invention comprise oligonucleotides of from about 9 to about 200 bases having homopolymer or heteropolymer sequences of nucleotides selected from the group consisting of adenylic acid (A), cytidylic acid (C), guanylic acid (G) or uridylic acid (U).

Particular oligonucleotide sequences used with the compounds of the present invention are selected on the basis of their desired target. The sequence selected hybridizes with the target nucleic acid. Exemplary targets include the MYC oncogene, the RAS oncogene, and viral nucleic acids.

The compounds of the present invention are preferably produced by a modification of the solid phase phosphoramidite method. *Oligonucleotide synthesis: Practical Approach*, ed. by M. J. Gait, pages 35–81, IRL Press, Washington, D.C. (1984).

In accordance with our modification of the solid phase method, a diol is introduced at one, or both, terminal(s) of the oligonucleotide by a procedure in which the diol is reacted with an alkoxytrityl compound to form a tritylated diol. The diol is preferably a glycol, more preferably, a polyalkyleneglycol. The alkoxytrityl reagent is preferably monomethoxytrityl chloride or dimethoxytrityl chloride and, most preferably dimethoxytrityl chloride. The tritylated diols are then reacted with a cyanophosphine reagent to form a trityldiolcyanophosphine compound, which compound is used as a phosphoramidite reagent (hereinafter referred to as a "diol phosphoramidite reagent") in the solid phase synthesis of the compounds of the present invention.

The initial step in solid phase synthesis is attachment of a nucleoside to a solid support, preferably a controlled pore glass (CPG) support. The nucleoside is preferably attached to the CPG via a succinate linkage at the 3'-hydroxyl position of the nucleoside. Other means of attaching nucleosides to solid supports are known and readily apparent to those of skill in the oligonucleotide synthesis art. Alternatively, in order to introduce a diol at the 3' terminal, a diol phosphoramidite reagent can be attached to the solid support prior to addition of the first nucleoside. The diol phosphoramidite reagent is attached to the solid support using succinate or other linkages in a manner analogous to methods used for nucleoside attachment. Means of modifying such methods for use with diol phosphoramidite reagents will be readily apparent to those of skill in the art. Any number of diols can be placed on the solid support prior to addition of the first nucleoside. Preferably from 1 to about 50 diols are used. Where diols are attached only to the 5' terminus, no diols are placed on the solid support.

Following attachment of the first nucleoside or the diol(s) to the solid support, chain elongation occurs via the sequential steps of removing the 5'-hydroxyl protecting group (a functionalized trityl group), activating the 5'-hydroxyl group in the presence of a phosphoramidite reagent, i.e., a 5'-trityl nucleoside, 3'-phosphoramidite, capping the unreacted nucleosides and oxidizing the phosphorous linkage.

The protecting group at the 5'-hydroxyl position of the attached nucleosides is removed with acid, preferably trichloroacetic acid.

Activating reagents that can be used in accordance with this method are well known to those of skill in the art. Preferred activating reagents are tetrazole and activator gold (Beckman Instr. Inc., Palo Alto, Calif.).

The activation step occurs in the presence of the added nucleoside phosphoramidite reagent or diol phosphoramidite reagent, which latter reagent replaces the nucleoside phosphoramidite reagent of conventional synthetic methods when diol is added to the terminal(s) of the polynucleotide. Unreacted chains are terminated or capped with capping reagents such as acetic anhydride and N-methyl amidizole.

The labile trivalent phosphorus linkage is oxidized, preferably with iodine, to the stable, pentavalent phosphodiester linkage of the oligonucleotide.

After the desired oligonucleotide chain assembly is complete, the phosphate protecting groups are removed, the chains are separated from the solid support and the base protecting groups are removed by conventional methods. Gaits, supra at 67–70.

Those skilled in the art will appreciate that other means of synthesizing oligonucleotides can be modified in an analogous manner to produce diol-terminated antisense oligonucleotides.

The compounds of the present invention are useful in treating mammals with hereditary disorders or diseases associated with altered genetic expression mechanisms. At present, attempts are underway to develop antisense therapies for use in treating viral infections such as HIV, cytomegalovirus, herpes simplex, hepatitis B, papilloma virus and picorna virus; cancers of the lung, cervix, colon, breast and ovary; inflammatory diseases; and diseases of the immune system such as acquired immunodeficiency syndrome (AIDS), hematological neoplasma, and hyperproliferative disorders. Armstrong, supra at 89; Klausner, supra at 303, 304.

Pharmaceutical compositions of the present invention comprise physiologically acceptable carriers and compounds comprising an oligonucleotide of from about 9 to about 200 bases having a diol at either or both termini.

The present invention includes one or more of the compounds of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate.

Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any needed preservatives, buffers or propellants as may be required. Opthalmic formulations, eye ointments, powders and solutions are also contemplated as being within the scope of this invention.

The present compounds can also be administered in the form of liposomes. As is known in the art, liposomes are generally derived from phospholipids or other lipid substances. Liposomes are formed by mono-or multi-lamellar hydrated liquid crystals that are dispersed in an aqueous medium. Any non-toxic, physiologically acceptable and metabolizable lipid capable for forming liposomes can be used. The present compositions in liposome form can contain, in addition to the lipoxygenase inhibiting compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, *Methods in Cell Biology*, Ed. by Prescott, Volume XIV, Academic Press, New York, N.Y., p. 33 et seq., (1976).

Actual dosage levels of active ingredient in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided does may be in amounts, for example, of from about 1 nanomol to about 5 micromols per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The following examples further illustrate the invention and are not to be construed as limiting of the specification and claims in any way.

EXAMPLE 1

Preparation of Tetraethyleneglycol-terminated Anti-RAS oncogene DNA a. Preparation of dimethoxytrityltetraethyleneglycol (DMTTEG)

An excess of tetraethyleneglycol TEG (about 100 mls) was admixed with about 7 mls (5.1 g; 40 mmols) of Hunig's base in a round bottom flask. About 3.08 g (10 mmols) of dimethoxytrityl chloride (DMTCl) was added to the TEG admixture and the DMTCl-TEG mixture maintained with constant stirring at room temperature (about 25° C.) for about 8 to 12 hours to form DMTTEG.

b. Preparation of dimethoxytrityltetraethyleneglycolcyanophosphine (DMTTEGCP)

Six grams of the DMTTEG from step (a) was admixed with 20 mls of dry dichloromethane. About 6.2 mls of Hunig's base was added to the admixture, followed by the dropwise addition of a chlorophosphine mixture to form DMTTEGCP. The chlorophosphine mixture was prepared by dissolving 1.67 g of 2-cyanoethyl N,N-diisopropylchlorophosphoramidite in 5 mls of dry dichloromethane.

c. Preparation of TEG-terminated Anti-RAS oncogene DNA

The oligodeoxynucleotides of Table 1 were prepared according to a modified solid phase phosphoramidite method. GAIT, supra. The oligodeoxynucleotides were synthesized from the 3' to the 5' terminus.

TABLE 1

| Sequence | | | | | | | | Ref. Code |
|---|---|---|---|---|---|---|---|---|
| 5' X | GGA | GCT | GGT | GGC | GTA | X | (A)3' | SRAS01 |
| 5' XX | GGA | GCT | GGT | GGC | GTA | XX | (A)3' | SRAS02 |
| 5' X | CCT | CGA | CCA | CCG | CAT | X | (A)3' | ASRAS01 |
| 5' XX | CCT | CGA | CCA | CCG | CAT | XX | (A)3' | ASRAS02 |
| 5' | CCT | CGA | CCA | CCG | CAT | | 3' | D89076 |

X is TEG
A, C, G & T represent the deoxynucleotides adenylic, cytidylic, guanidylic and thymidylic acids, respectively.

Either the nucleoside adenosine (SRASOI, SRAS02, ASRAS01, ASRAS02) or thymidine was attached (D89076) to a CPG solid support using a succinate linkage. GAIT, supra. The synthesis of D89076 proceeded in accordance with standard solid phase phosphoramidite procedures. In sequences SRASOI, SRAS02, ASRAS01 and ASRAS02, synthesis proceeded in accordance with a modified phosphoramidite procedure. The 5' hydroxyl group of the attached adenosine nucleoside was reacted with trichloroacetic acid to deprotect the 5' hydroxyl group. Following this deprotection step, the attached adenosine nucleoside was reacted with the activating agent, tetrazole, and a phosphoramidite reagent comprising DMTTEGCP, prepared by the processes of steps a and b above. The activation step was followed by the capping of unreacted 5' hydroxyl groups with acetic an hydride and N-methylimidazole. The phosphorous linkage was then oxidized with iodine in accordance with standard procedures.

In sequences SRAS02 and ASRAS02, containing two TEG residues, the deprotecting, activating, capping and oxidizing steps were repeated as described above. Chain elongation proceeded via the sequential steps of deprotection, activation, capping and oxidation as described above with the modification that the desired nucleoside phosphoramidite reagent was substituted for the DMTTEGCP during the activation step. Following attachment of the last desired nucleoside, either one or two TEG residues were attached at the 5' terminal in a manner analogous to the attachment of TEG at the 3' terminus.

At the end of chain assembly, the DNA strand was removed from the CPG support with concentrated ammonium hydroxide. The solution was then further treated at 55° C. for 8 to 15 hours to remove all the protecting groups on the exocyclic amines of the bases.

EXAMPLE 2

Preparation of hexaethyleneglycol (HEG)-terminated Anti-RAS oncogene DNA

Hexaethyleneglycol (HEG) terminated anti-RAS oncogene DNA was prepared according to the methods of Example 1. HEG was reacted with DMTCl to form DMTHEG. The DMTHEG was then reacted with a cyanophosphine compound to form DMTHEGCP, which was used in the modified solid phase phosphoramidite synthesis method of Example 1(c) to form HEG-terminated anti-RAS oncogene DNA.

TABLE 2

| Sequence | | | | | | | |
|---|---|---|---|---|---|---|---|
| 5' X | GGA | GCT | GGT | GGC | GTA | X | (A)3' |
| 5' XX | GGA | GCT | GGT | GGC | GTA | XX | (A)3' |
| 5' X | CCT | CGA | CCA | CCG | CAT | X | (A)3' |
| 5' XX | CCT | CGA | CCA | CCG | CAT | XX | (A)3' |
| 5' | CCT | CGA | CCA | CCG | CAT | | 3' |

X is HEG
A, C, G & T represent the deoxynucleotides adenylic, cytidylic, guanidylic and thymidylic acids, respectively.

EXAMPLE 3

Nuclease Resistance of TEG-terminated Anti-RAS Oncogene DNA

The oligonucleotides of Table 1 were dissolved in water. DNA concentrations were then determined by measuring the absorbance of samples at 260 nm (on a Perkin Elmer Lambda 4C Spectrophotometer at ambient room temperature) and using calculated extinction coefficients [method of Cantor and Warsaw, *CRC*

Handbook of Biochemistry and Molecular Biology. 3rd. ed. Vol. 1, CRC Press, page 589 (1975)].

Oligonucleotides were incubated for 2 hours at 37° C. at a total strand concentration of 6 or 7 mM in cell culture medium containing RPMI 1640; 20 mM N-(2-hydroxyethyl) piperazine-N'-(2-ethanesulfonic acid), pH 7.4; and 10% fetal calf serum (FCS) (GIBCO Laboratories, Grand Island, N.Y.). The FCS was heat inactivated at 56° C. for 0.5 hours prior to use. Samples were then placed on ice and deproteinized using five extractions with 24:1 chloroform:isoamyl alcohol. Samples were either stored frozen at −20° C. or immediately loaded onto a refrigerated (4° C.) WISP (Waters) HPLC autoinjector.

Oligonucleotide hydrolysis was quantitated by determining the amount of disappearance of the parent compound. Oligonucleotides (from the reaction mixture) were separated on an LKB Ultrachrome GTi dual pump chromatography system equipped with a fixed wavelength detector (260 nm), and recording integrator, using a GenPak FAX (Waters) anion exchange column equilibrated in Buffer A (1 mM EDTA; 15 mM sodium phosphate, pH 8.5). Column temperature was maintained at 60° C. using a Waters column oven. Fifty microliter sample injection volumes were used. The oligonucleotides were eluted using a linear gradient of 0% to 100% Buffer B (Buffer A containing 0.5M NaCl) over 60 minutes. Buffer flow rate was 1 mL/min.

Following incubation (2 hrs) in the presence of fetal calf serum-associated exonuclease, no degradation of compounds SRAS01 or ASRAS02 was observed (Table 2, see % degradation of major peak). During a similar incubation period, 87.0% and 82.1% of ASRAS01 and SRAS02, respectively, remained. In comparison, only 24.7% of oligomer D89076 remained after the same incubation period.

TABLE 3

| 0 SAMPLE ID | 1 AREA-MAJOR PEAK/0.0 MIN | 2 AREA-MAJOR PEAK/2.0 HR | 3% DEGRADATION MAJOR PEAK |
|---|---|---|---|
| 1 SRAS01 | 0.2325 | 0.3663 | 0.0 |
| 2 ASRAS01 | 0.3744 | 0.3258 | 13.0 |
| 3 SRAS02 | 0.2164 | 0.1777 | 17.9 |
| 4 ASRAS02 | 0.3642 | 0.3697 | 0.0 |
| 5 D89076 | 1.2861 | 0.3177 | 75.3 |

All four TEG-oligomers were resistant to hydrolysis by the FCS-associated exonucleases. The bis-diTEG-oligomers (SRAS01 and ASRAS02) appeared to be completely resistant to hydrolysis. TEG-derivatized oligodeoxynucleotides represent significant improvements over unmodified compounds in terms of resistance to exonuclease hydrolysis.

EXAMPLE 4

Ability of TEG-Antisense Oligomers to Protein Expression and Growth in Human Tumor Cell Lines and PHA Stimulation of Peripheral Blood Lymphocytes It has been demonstrated by others (Heikkila, R. et al., *Nature*, 328:445–449, 1987) that unmodified antisense oligonucleotides directed towards the initiation codon region of the c-myc oncogene could inhibit the expression of c-myc protein in PHA stimulated peripheral blood lymphocytes (PBL) resulting in a block in the progression of cells into the S-phase of the cell cycle. C-myc directed antisense DNA was also shown to inhibit the growth of HL-60 human erytholeukemia cells in vitro (Wickstrom, E. L., et al., *Proc. Natl. Acad. Sci. USA*, 85:1028–1032, 1988). We directly compared the sequences of Table 4 for their ability to inhibit tumor cell growth, to downregulate cmyc expression, and to inhibit the progression of PHA stimulated PBL into the S-phase of the cell cycle.

TABLE 4

UNMODIFIED C-MYC ANTISENSE SEQUENCE
5' ACC GTT GAG GGG CAT 3'
MODIFIED C-MYC ANTISENSE SEQUENCE
5' XX AAC GTT GAG GGG CAT XX A 3'
(X = TEG)

a. Comparison of the Effect of Modified (with TEG) and Non-Modified C-MYC Antisense DNA on the Progression of PHA Stimulated PBL Into the S-Phase of the Cell Cycle Human PBL's were stimulated with PHA for 48 hours in the presence or absence of the antisense oligonucleotide sequences of Table 4. The percent of the population of cells in each treatment group in the S-phase of the cell cycle as compared to the nontreated control was determined using standard flow cytometric techniques. The results are shown in Table 5.

TABLE 5

| OLIGONUCLEOTIDE | CONCENTRATION ($\mu$M) | % CONTROL S-PHASE |
|---|---|---|
| NONE |  | 100 |
| 5' AAC GTT GAG GGG CAT 3' | 30 | 75 ± 6 |
|  | 60 | 9 ± 10 |
| 5' XX AAC GTT GAG GGG CAT XX A 3' | 30 | 80 ± 4 |
|  | 60 | <6 |

The data show that the presence of TEG at both the 3' and 5' termini does not alter the inhibitory effect of the antisense DNA.

b. Comparison of the Effect of Modified (with TEG) and Non-Modified C-MYC Antisense DNA on C-MYC Protein Expression in MOLT-4 Human T-Cell Leukemia Cells Asynchronus exponentially growing Molt-4 cells were incubated for 8 hours in the presence or absence of 60 $\mu$M c-myc directed antisense DNA. The cells were then incubated for 45 minutes in the presence of $^{35}$S-methionine and the content of c-myc protein quantitated using radioimmunoprecipitation with a c-myc antibody.

The results are displayed in Table 6.

TABLE 6

| OLIGONUCLEOTIDE | CONCENTRATION (μM) | % REDUCTION C-MYC PROTEIN |
|---|---|---|
| NONE | | 0 |
| 5'    AAC GTT GAG GGG CAT 3' | 60 | 61.0 ± 2.6 |
| 5' XX  AAC GTT GAG GGG CAT XX A 3' | 60 | 67.9 ± 0.7 |

The TEG containing antisense DNA was slightly more potent than the unmodified antisense DNA.

c. Comparison of the Effect of Modified (with TEG) and Unmodified C-MYC Antisense DNA to Inhibit the Growth of Human CCRF-CEM T-Cell Leukemia Cell Growth in Vitro Asynchronus exponentially growing CCRF-CEM cells were incubated for 48 hours in the presence or absence of antisense DNA and then cell numbers determined in each treatment group. The concentration of antisense DNA required to inhibit cell growth by 50% was then determined (IC$_{50}$) Both of the modified and non-modified antisense DNAs of Table 3 displayed approximately equivalent (IC$_{50}$) concentrations of 40 μM.

These data demonstrate that the presence of TEG at the 3' and 5' termini of antisense DNA does not affect the ability of such antisense DNA to hybridize with and inhibit the function of target nucleic acids.

EXAMPLE 5

Additional Exonuclease Stable Oligonucleotides

The exonuclease stable digonucleotides set forth in Table 7 were prepared according to the methods of Example 1.

TABLE 7

```
5' XX  A—ACG—TTG—AGG—GGC—ATX—XA                    3'
   XX  GCC—CGC—CTC—GGT—CCC—CGC—CCX—XA
   XX  GGG GCG GAG TTA GGG GCG GCG GGX XA
   XX  GGG—GAG—GAG—GGA—GGG—GAG—GGA—XXA
   XX  GGG—GAG—GTG—GGT—GGG—GAG—GGT—XXA
       AAG GTT GAG GGG CAT XXA
   X   AA—CGT—TGA—GGG—GCA—TTX—A
   XX  TTC—GCT—TAC—CAG—AGT=XXA
   XX  GCG—GGA—GGC—TGC—TGG—XXA
   XX  GGA—GGC—TGC—TGG—AGC—XXA
   XX  CAA—GTT—CAT—AGG—TGA—TTG—CTC—XXA
   AL—CAC—TCC—TTT—AGC—AAG—XXA
   AL—GAA—CGA—TTT—CCT—CAC—XXA
   XX  CTC—ACT—GCC—GCG—CAT—XXA
   XX  GGG—TCT—TCG—GGC—CAT—XXA
   XX  GTC—GAC—CGG—TTC—CAT—XXA
   XX  TGT—AAC—TGC—TAT—AAA—XXA
   XX  GTT—CCT—CCT—CTT—TAA—XXA
   XX  TAC—TGA—CTT—ATA—TTT—XXA
   XX  TAC—TGA—CTT—ATA—TTT—XXA
   XX  TTT—ATA—TTC—AGT—CAT—XXA
   XX  TGG—GGA—GGG—TGG—GGA—GGG—TGG—GGA—AGG—XXA
   XX  CTT—ATA—TTC—CGT—CAT—XXA
   XX  TAA—CGC—CTA—TTC—TGC—XXA
   XX  CGT—CTT—ATC—CGC—AAT—XXA
   XX  TTG—CTC—TCC—TCT—GTC—XXA
   XX  CTG—TCT—CCT—CTC—GTT—XXA
   XX  ATC—TAC—TGG—CTC—CAT—XXA
   XX  TAC—CTC—GGT—CAT—CTA—XXA
   XX  ACA—CCC—AAT—TCT—GAA—ATG—GXX—A
   XX  GGT—AAA—GTC—TTA—ACC—CAC—AXX—A
   XX  TAC—GGG—GAG—TTG—CAA—XXA
   X is TEG
```

We claim:

1. A nuclease resistant compound consisting of an oligonucleotide sequence of from about 12 to about 25 bases having an alkylene diol at either or both termini.

2. A compound according to claim 1 wherein the diol is a polyalkyleneglycol.

3. A compound according to claim 2 wherein the polyalkyleneglycol is a polyethyleneglycol.

4. A compound according to claim 3 wherein the polyethyleneglycol is hexaethyleneglycol.

5. A compound according to claim 3 wherein the polyethyleneglycol is tetraethyleneglycol.

6. A compound according to claim 1 wherein the obligonucleotide sequence has from about 15 to about 18 bases.

7. A DNA compound consisting of an oligonucleotide of the formula:

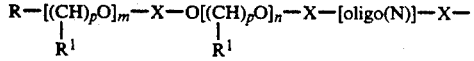

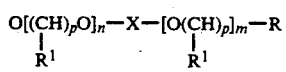

where
R is OH;
R$^1$ is hydrogen or C$_1$-C$_{12}$ alkyl;
X =

oligo (N) is an oligodeoxyribonucleotide sequence of from about 12 to about 25 bases;

m is independently 0 to 50 with the proviso that at least one m be 1 to 50;

n is independently 0 to 50; and p is independently 0 to 4 with the proviso that at least one p be 2 to 4.

8. A compound according to claim 7, wherein the oligo (N) is a homopolymer or heteropolymer sequence containing any combination of deoxyadenylic acid, deoxycytidylic acid, deoxyguanidylic acid or thymidylic acid.

9. A compound according to claim 7, wherein the oligo (N) is a homopolymer or heteropolymer sequence containing any combination of adenylic acid, cytidylic acid, guanidylic acid or uridylic acid.

10. A compound according to claim 7 wherein m and n are independently 1 to 8.

11. A compound according to claim 7 wherein both m and n are 4.

12. A compound according to claim 7 wherein both m and n are 6.

13. A compound according to claim 7 wherein the oligonucleotide sequence is from about 15 to about 18 bases.

14. A compound consisting of an oligonucleotide of the formula:

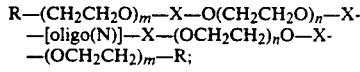

where
R is OH;
X=

oligo (N) is an oligodeoxyribonucleotide sequence of from about 12 to about 25 bases;

m is independently 0 to 50 with the proviso that at least one m be 1 to 50; and n is independently 0 to 50.

15. A compound according to claim 14, wherein the oligo (N) is a homopolymer or heteropolymer sequence containing any combination of deoxyadenylic acid, deoxycytidylic acid, deoxyguanidylic acid or thymidylic acid.

16. A compound according to claim 14 wherein m and n are independently 1 to 8.

17. A compound according to claim 14 wherein both m and n are 4.

18. A compound according to claim 14 wherein both m and n are 6.

19. A compound according to claim 14 wherein the oligonucleotide sequence is from about 15 to about 18 bases.

20. A pharmaceutical composition for inhibition of gene expression comprising a nuclease resistant compound which consists of an oligodeoxyribonucleotide sequence of from about 12 to about 25 bases having an alkylene diol at either or both termini and a physiologically acceptable carrier.

21. A composition according to claim 20 wherein the diol is a polyalkyleneglycol.

22. A composition according to claim 20 wherein the diol is polyethyleneglycol.

23. A composition according to claim 20 wherein the diol is hexaethyleneglycol or tetraethyleneglycol.

24. A pharmaceutical composition according to claim 20 wherein the compound consists of an oligonucleotide of the formula:

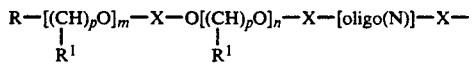

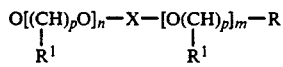

where
R is OH;
$R^1$ is hydrogen or $C_1$-$C_{12}$ alkyl;
X=

oligo (N) is an oligodeoxyribonucleotide sequence of from about 12 to about 25 bases;

m is independently 0 to 50 with the proviso that at least 1 m be 1 to 50;

n is independently 0 to 50; and p is independently 0 to 4 with the proviso that at least one p be 2 to 4.

25. A composition according to claim 24 wherein the oligo (N) is a homopolymer or heteropolymer sequence containing any combination of deoxyadenylic acid, deoxycytidylic acid, deoxyguanidylic acid or thymidylic acid.

26. A compound of the formula:

where X is tetraethyleneglycol; and n is 1 or 2.

* * * * *